(12) United States Patent
Dellinger et al.

(10) Patent No.: US 7,790,387 B2
(45) Date of Patent: *Sep. 7, 2010

(54) THIOCARBONATE LINKERS FOR POLYNUCLEOTIDES

(75) Inventors: Douglas J. Dellinger, Boulder, CO (US); Zoltan Timar, Boulder, CO (US); Joel Myerson, Berkeley, CA (US); Geraldine Dellinger, Boulder, CO (US); Marvin H. Caruthers, Boulder, CO (US)

(73) Assignees: Agilent Technologies, Inc., Santa Clara, CA (US); Regents of the University of Colorado, Denver, CO (US)

( * ) Notice: Subject to any disclaimer, the term of this patent is extended or adjusted under 35 U.S.C. 154(b) by 211 days.

This patent is subject to a terminal disclaimer.

(21) Appl. No.: 11/903,821

(22) Filed: Sep. 24, 2007

(65) Prior Publication Data

US 2009/0082554 A1    Mar. 26, 2009

(51) Int. Cl.
*C12Q 1/68* (2006.01)
*C07H 21/00* (2006.01)
*C07H 21/02* (2006.01)

(52) U.S. Cl. .................. 435/6; 536/23.1; 536/24.3; 536/24.33; 536/25.3

(58) Field of Classification Search .......... 435/6; 536/23.1, 24.3, 24.33, 25.3
See application file for complete search history.

(56) References Cited

U.S. PATENT DOCUMENTS

| | | | |
|---|---|---|---|
| 5,859,233 | A | 1/1999 | Hirschbein et al. |
| 6,222,030 | B1 | 4/2001 | Dellinger et al. |
| 6,630,581 | B2 | 10/2003 | Dellinger et al. |
| 6,673,918 | B2 | 1/2004 | Bellon et al. |
| 7,101,986 | B2 | 9/2006 | Dellinger et al. |
| 7,135,565 | B2 | 11/2006 | Dellinger et al. |
| 7,193,077 | B2 | 3/2007 | Dellinger et al. |
| 7,271,258 | B2 | 9/2007 | Dollinger et al. |
| 2005/0048497 | A1 | 3/2005 | Dellinger et al. |
| 2005/0048601 | A1 | 3/2005 | Dellinger et al. |
| 2005/0049407 | A1 | 3/2005 | Dellinger et al. |
| 2005/0136477 | A1 | 6/2005 | Akhavan-Tafti |
| 2005/0287555 | A1 | 12/2005 | Dellinger et al. |
| 2006/0247430 | A1 | 11/2006 | Dellinger et al. |
| 2007/0099859 | A1 | 5/2007 | Dellinger et al. |
| 2007/0100136 | A1 | 5/2007 | Dellinger et al. |
| 2007/0100137 | A1 | 5/2007 | Dellinger et al. |
| 2007/0100138 | A1 | 5/2007 | Dellinger et al. |

OTHER PUBLICATIONS

McIsaac, J.E. et al. The nucleophilic reactivity of peroxy anions. Journal of Organic Chemistry. 1972, vol. 37, No. 7, pp. 1037-1041.

*Primary Examiner*—Jezia Riley

(57) ABSTRACT

In various embodiments of the invention, novel compositions having a polynucleotide bound to a substrate via a cleavable linker are provided, and methods of cleaving a polynucleotide from a substrate are provided.

26 Claims, No Drawings

US 7,790,387 B2

THIOCARBONATE LINKERS FOR POLYNUCLEOTIDES

INTRODUCTION

Solid phase chemical synthesis of DNA fragments is routinely performed using protected nucleoside phosphoramidites. Beaucage et al. (1981) Tetrahedron Lett. 22:1859. In this approach, the 3'-hydroxyl group of an initial 5'-protected nucleoside is first covalently attached to the polymer support. Pless et al. (1975) Nucleic Acids Res. 2:773. Synthesis of the oligonucleotide then proceeds by deprotection of the 5'-hydroxyl group of the attached nucleoside, followed by coupling of an incoming nucleoside-3'-phosphoramidite to the deprotected hydroxyl group. Matteucci et al. (1981) J. Am. Chem. Soc. 103:3185. The resulting phosphite triester is finally oxidized to a phosphotriester to complete one round of the synthesis cycle. Letsinger et al. (1976) J. Am. Chem. Soc. 98:3655. The steps of deprotection, coupling and oxidation are repeated until an oligonucleotide of the desired length and sequence is obtained. Optionally, after the coupling step, the product may be treated with a capping agent designed to esterify failure sequences and cleave phosphite reaction products on the heterocyclic bases.

Solid phase polynucleotide synthesis results in a polynucleotide bound upon a solid support. Typically, an additional step releases the polynucleotide from the solid support after the polynucleotide strand has been synthesized. This release step yields the polynucleotide in solution, which may then be separated from the solid support, e.g., by filtration or other suitable methods. The release step is dependent upon having a support that is functionalized with a releasable moiety that, while inert under the conditions used in the synthesis cycle, provides for the release of the synthesized polynucleotide under conditions conducive for doing so.

While there are examples of cleavable linkers in the literature, there remains a need for additional cleavable linkers for polynucleotides, e.g. polynucleotides bound to a substrate.

SUMMARY

Aspects of the invention include polynucleotides bound to a substrate via a cleavable thiocarbonate linker. The thiocarbonate cleavable linkers are cleavable under conditions that include contact with an α-effect nucleophile. Also provided are methods of cleaving a polynucleotide bound to a substrate via a thiocarbonate linker, where such methods may include pre- or post cleavage polynucleotide modification. Additional aspects of the invention include polynucleotide products produced by the subject methods.

DEFINITIONS

In this specification and in the claims that follow, reference will be made to a number of terms that shall be defined to have the following meanings unless a contrary intention is apparent:

A "nucleotide" refers to a sub-unit of a nucleic acid (whether DNA or RNA or analogue thereof) which includes a phosphate group, a sugar group and a heterocyclic base, as well as analogs of such sub-units. A "nucleoside" references a nucleic acid subunit including a sugar group and a heterocyclic base. A "nucleoside moiety" refers to a portion of a molecule having a sugar group and a heterocyclic base (as in a nucleoside); the molecule of which the nucleoside moiety is a portion may be, e.g. a polynucleotide, oligonucleotide, or nucleoside phosphoramidite. A "nucleobase" references the heterocyclic base of a nucleoside or nucleotide. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected.

As used herein, polynucleotides include single or multiple stranded configurations, where one or more of the strands may or may not be completely aligned with another. The terms "polynucleotide" and "oligonucleotide" are generic to polydeoxynucleotides (containing 2-deoxy-D-ribose), to polyribonucleotides (containing D-ribose), to any other type of polynucleotide having nucleotide subunits that are N-glycosides of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 200 nucleotides in length, while a "polynucleotide" includes a nucleotide multimer having at least two nucleotides and up to several thousand (e.g., 5000, or 10,000) nucleotides in length. It will be appreciated that, as used herein, the terms "nucleoside", "nucleoside moiety" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "modified alkyl" refers to an alkyl group having from one to twenty-four carbon atoms, and further having additional groups, such as one or more linkages selected from ether-, thio-, amino-, phospho-, keto-, ester-, and amido-, and/or being substituted with one or more additional groups including lower alkyl, aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl. The term "modified lower alkyl" refers to a group having from one to eight carbon atoms and further having additional groups, such as one or more linkages selected from ether-, thio-, amino-, phospho-, keto-, ester- and amido-, and/or being substituted with one or more groups including lower alkyl; aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more typically selected from the group consisting of lower alkyl, modified lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azido, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings.

The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j—Ar wherein j is an integer in the range of 1 to 24, more typically 1 to 6, and Ar is a monocyclic aryl moiety.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocyclic group consists of carbon atoms and from one to four heteroatoms selected from the group consisting of nitrogen, oxygen and sulfur. As used herein, the term "nitrogen heteroatoms" includes any oxidized form of nitrogen and the quaternized form of nitrogen. The term "sulfur heteroatoms" includes any oxidized form of sulfur. Examples of heterocyclic groups include purine, pyrimidine, piperidinyl, morpholinyl and pyrrolidinyl. "Heterocyclic base" refers to any natural or non-natural heterocyclic moiety that can participate in base pairing or base stacking interaction on an oligonucleotide strand.

The term "halo" or "halogen" is used in its conventional sense to refer to a chloro, bromo, fluoro or iodo substituent.

A "phospho" group includes a phosphodiester, phosphotriester, and H-phosphonate groups. In the case of either a phospho or phosphite group, a chemical moiety other than a substituted 5-membered furyl ring may be attached to 0 of the phospho or phosphite group which links between the furyl ring and the P atom.

By "protecting group" as used herein is meant a species which prevents a portion of a molecule from undergoing a specific chemical reaction, but which is removable from the molecule following completion of that reaction, as taught for example in Greene, et al., "Protective Groups in Organic Synthesis," John Wiley and Sons, Second Edition, 1991. A "peroxyanion-labile linking group" is a linking group that releases a linked group when contacted with a solution containing peroxyanions. Similarly, a "peroxyanion-labile protecting group" is a protecting group that is removed from the corresponding protected group when contacted with a solution containing peroxyanions. As used herein, "2'-O protecting groups" or "2'-hydroxyl protecting groups" are protecting groups which protect the 2'-hydroxyl groups of the polynucleotide (e.g. bound to the 2'-O). As used herein, "phosphorus protecting group" (sometimes referenced as "phosphate protecting group") references a protecting group which protects a phosphorus group (e.g. is bound to a phosphorus group wherein the phosphorus group is attached to a sugar moiety of, e.g. a nucleotide, a nucleoside phosphoramidite, a polynucleotide intermediate, or a polynucleotide). As used herein, "cleaving", "cleavage", "deprotecting", "releasing", or like terms when used in reference to a protecting group refers to breaking a bond via which the protecting group is bound to the protected group, resulting in the cleaved protecting group and the deprotected moiety (the moiety that was the protected group when bound to the protecting group).

The term "electron withdrawing" denotes the tendency of a substituent to attract valence electrons of the molecule of which it is a part, i.e., an electron-withdrawing substituent is electronegative with respect to neighboring atoms. A quantification of the level of electron-withdrawing capability is given by the Hammett sigma constant. This well known constant is described in many references, for instance, March, Advanced Organic Chemistry 251-59, McGraw Hill Book Company, New York, (1977). Exemplary electron-withdrawing groups include nitro, acyl, formyl, sulfonyl, trifluoromethyl, cyano, chloride, and the like.

The term "electron-donating" refers to the tendency of a substituent to repel valence electrons from neighboring atoms, i.e., the substituent is less electronegative with respect to neighboring atoms. Exemplary electron-donating groups include amino, methoxy, alkyl (including alkyl having a linear or branched structure, alkyl having one to eight carbons), cycloalkyl (including cycloalkyl having four to nine carbons), and the like.

The term "alpha effect," as in an "alpha effect nucleophile" in a deprotection/oxidation agent, is used to refer to an enhancement of nucleophilicity that is found when the atom adjacent a nucleophilic site bears a lone pair of electrons. As the term is used herein, a nucleophile is said to exhibit an "alpha effect" if it displays a positive deviation from a Bronsted-type nucleophilicity plot. Hoz et al. (1985) Israel J. Chem. 26:313. See also, Aubort et al. (1970) Chem. Comm. 1378; Brown et al. (1979) J. Chem. Soc. Chem. Comm. 171; Buncel et al. (1982) J. Am. Chem. Soc. 104:4896; Edwards et al. (1962) J. Am. Chem. Soc. 84:16; Evanseck et al. (1987) J. Am. Chem. Soc. 109:2349. The magnitude of the alpha effect is dependent upon the electrophile which is paired with the specific nucleophile. McIsaac, Jr. et al. (1972), J. Org. Chem. 37:1037. Peroxy anions are example of nucleophiles which exhibit strong alpha effects.

"Moiety" and "group" are used interchangeably herein to refer to a portion of a molecule, typically having a particular functional or structural feature, e.g. a linking group (a portion of a molecule connecting two other portions of the molecule), or an ethyl moiety (a portion of a molecule with a structure closely related to ethane).

"Linkage" as used herein refers to a first moiety bonded to two other moieties, wherein the two other moieties are linked via the first moiety. Typical linkages include ether (—O—), keto (—C(O)—), amino (—NH—), amido (—N—C(O)—), thio (—S—), phosphate (—PO$_4$H—), ester (—O—(C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, and modified lower alkyl.

A "group" includes both substituted and unsubstituted forms. Typical substituents include one or more lower alkyl, amino, imino, amido, alkylamino, arylamino, alkoxy, aryloxy, thio, alkylthio, arylthio, alkyl; aryl, thioalkyl, hydroxyl, mercapto, halo, cyano, nitro, nitroso, azido, carboxy, sulfide, sulfonyl, sulfoxy, phosphoryl, silyl, silyloxy, and boronyl optionally substituted on one or more available carbon atoms with a nonhydrocarbyl substituent such as cyano, nitro, halogen, hydroxyl, sulfonic acid, sulfate, phosphonic acid, phosphate, or phosphonate or the like. Any substituents are typically chosen so as not to substantially adversely affect reaction yield (for example, not lower it by more than 20% (or 10%, or 5% or 1%) of the yield otherwise obtained without a particular substituent or substituent combination).

As used herein, "dissociation constant," e.g., an acid dissociation constant, has its conventional definition as used in the chemical arts and references a characteristic property of a molecule having a tendency to lose a hydrogen ion. The value of a dissociation constant mentioned herein is typically expressed as a negative $\log_{10}$ value, i.e., a pKa (for an acid dissociation constant).

Hyphens, or dashes, are used at various points throughout this specification to indicate attachment, e.g., where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g., a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g., where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

DETAILED DESCRIPTION

Aspects of the invention include polynucleotides bound to a substrate via a cleavable thiocarbonate linker. The thiocarbonate cleavable linkers are cleavable under conditions that include contact with an α-effect nucleophile. Also provided are methods of cleaving a polynucleotide bound to a substrate via a thiocarbonate linker, where such methods may include pre- or post cleavage polynucleotide modification. Additional aspects of the invention include polynucleotide products produced by the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In certain embodiments of the present invention, a composition is provided having a polynucleotide bound to a substrate via a thiocarbonate cleavable linker. In certain embodiments, the thiocarbonate cleavable linker has the structure (I):

wherein:
  Lnk is a linking group;
  Sub denotes the site at which the substrate is attached to the cleavable linker; and
  RPN denotes the site at which the polynucleotide is attached to the cleavable linker.

The polynucleotide attached to the substrate via the cleavable linker may be any polynucleotide, for example DNA, RNA, a polynucleotide analog, a modified polynucleotide, a polynucleotide having protecting groups (e.g., protecting groups bound to the amine groups of nucleobases, protecting groups bound to the phosphate groups of the polynucleotide, protecting groups which protect hydroxyl groups of the polynucleotide (e.g., bound to the 2'-O), or other protecting groups). The polynucleotide may be synthesized in situ (e.g. synthesized one nucleotide at a time using polynucleotide synthesis schemes well known in the art) or may be separately synthesized and then attached to the substrate via the cleavable linker. For example, a modified cleavable linker moiety is bound to the substrate, wherein the modified cleavable linker moiety has a protected nucleotide moiety bound to a cleavable linker moiety as described herein. The protected nucleotide moiety is then deprotected, and the deprotected nucleotide moiety serves as a site to either start in situ synthesis of a full length polynucleotide or as a site for attachment of an already synthesized polynucleotide. Other methods of providing the polynucleotide attached to the substrate via the cleavable linker are possible and may be employed in accordance with the present invention. The polynucleotide may generally be attached to the cleavable linker via any available site of the polynucleotide, e.g. at the 2'-O, the 3'-O, the 5'-O, an amino group of a nucleobase, or any other site, given that the available site provides a resulting structure that is cleavable upon contacting the polynucleotide-bound substrate with the α-effect nucleophile. Typically, the polynucleotide is attached to the cleavable linker at the 2'-O or the 3'-O, less typically at the 5'-O or at an amino group of a nucleobase.

In certain embodiments, the polynucleotide has a 2'-hydroxyl protecting group and at least one additional protecting group selected from a nucleobase protecting group and a phosphorus protecting group, wherein said 2'-hydroxyl protecting group is characterized as stable under conditions which include an α-effect nucleophile; and wherein said at least one additional protecting group is characterized as labile under conditions which include an α-effect nucleophile.

In certain embodiments, the polynucleotide has a 2'-hydroxyl protecting group, a phosphorus protecting group, and a nucleobase protecting group, wherein the 2'-hydroxyl protecting group and phosphate protecting group are characterized as stable under conditions which include an α-effect nucleophile; and wherein the nucleobase protecting group is characterized as labile under conditions which include an α-effect nucleophile.

Referring to structure (I), the linking group -Lnk- is selected from (1) a linking group linking the substrate and the cleavable linker; or (2) a covalent bond between the substrate and the cleavable linker (e.g. the cleavable linker is directly bound to the substrate). In particular embodiments, the linking group -Lnk- may be any appropriate linking group via which the substrate is attached to the cleavable linker. The linking group -Lnk- is typically selected from (1) a lower alkyl group; (2) a modified lower alkyl group in which one or more linkages selected from ether-, thio-, amino-, keto-, ester-, and amido- is present; (3) a modified lower alkyl substituted with one or more groups including lower alkyl; aryl, aralkyl, alkoxyl, thioalkyl, hydroxyl, amino, amido, sulfonyl, halo; or (4) a modified lower alkyl substituted with one or more groups including lower alkyl; alkoxyl, thioalkyl, hydroxyl, amino, amido, sulfonyl, halo, and in which one or more linkages selected from ether-, thio-, amino-, keto-, ester-, and amido- is present. The linking group -Lnk- may be bonded to the substrate at any position of the linking group -Lnk- available to bind to the substrate. Similarly, the linking group -Lnk- may be bonded to the adjacent cleavable linker at any position of the linking group -Lnk- available to bind to the adjacent cleavable linker. In certain embodiments, the linking group -Lnk- is a single methylene group, e.g. —$CH_2$—, or may be an alkyl group or modified alkyl group up to about 24 carbons long (and which may be straight-chain or branched-chain). In certain such embodiments, one or more linkages selected from ether, keto-, thio-, and amino- is present in the straight- or branched chain modified alkyl group. In an embodiment, the linking group -Lnk- comprises optionally substituted ethoxy, propoxy, or butoxy groups (i.e. may include the structure —$\{(CH_2)_m—O\}_n$—, wherein m is a integer selected from 2, 3, 4, and n is a integer selected from 1, 2, 3, 4, 5, 6). In an embodiment, the linking group -Lnk- has the structure —$(CH_2)_m$-Lkg-$(CH2)_n$-, wherein m and n are integers independently selected from the range of 1 to about 12, e.g. from the range of 2 to about 8, and Lkg is a linkage selected from ether-, thio-, amino-, keto-, ester-, and amido-.

In particular embodiments, the linking group -Lnk- has a first terminal site and a second terminal site. In such embodiments, the linking group -Lnk- is bound to the substrate at the first terminal site, and the linking group -Lnk- is bound to the cleavable linker at the second terminal site. The first and second terminal sites will depend on the design of the linking group taking into consideration, for example, the method used to attach the cleavable linker to the substrate.

The cleavable linker may be attached to a suitable substrate that may have a variety of forms and compositions. The substrate may derive from naturally occurring materials, naturally occurring materials that have been synthetically modified, or synthetic materials. Examples of suitable support materials include, but are not limited to, nitrocellulose, glasses, silicas, teflons, and metals (e.g., gold, platinum, and the like). Suitable materials also include polymeric materials, including plastics (for example, polytetrafluoroethylene, polypropylene, polystyrene, polycarbonate, and blends thereof, and the like), polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, and the like.

The cleavable linker may be bound directly to the substrate (e.g., to the surface of the substrate, e.g. to a functional group on the surface) or indirectly bound to the substrate, e.g., via one or more intermediate moieties (e.g., linking groups) and/or surface modification layer on the substrate. The nature of the site on the substrate to which the cleavable linker is attached (e.g., directly or via a linking group) is not essential to the present invention, as any known coupling chemistry compatible with the sensor substrate (i.e. which doesn't result in significant degradation of the sensor substrate) may be used to couple to the cleavable linker. As such, various strategies of coupling the cleavable linker to substrates using functional groups on the substrates are known in the art and may be employed advantageously in the disclosed methods. Typical strategies require a complementary reactive group on the cleavable linker or are selected based on moieties already present on the cleavable linker (e.g., amino groups, hydroxyl groups, or other functional groups), for example an active group on the substrate that is capable of reacting with a corresponding reactive group attached to the linker to result in the linker covalently bound to the substrate.

Accordingly, in certain embodiments of the present invention, a method is provided wherein the method includes: contacting a polynucleotide bound to a substrate via a thiocarbonate cleavable linker of the invention with a solution comprising an α-effect nucleophile to result in cleavage of the polynucleotide from the substrate; wherein the cleavable linker has the structure (I), as described above.

As mentioned above, embodiments of the present disclosure include methods for cleaving a polynucleotide from a substrate, wherein the polynucleotide is bound to a cleavable linker such as those described herein. In particular embodiments, the method includes contacting the polynucleotide bound to the substrate via the cleavable linker with a solution of an α-effect nucleophile (e.g., a peroxyanion solution), where the α-effect nucleophile has a pKa of about 4 to 13. In addition, the solution is at a pH of about 6 to 11.

In particular embodiments, a polynucleotide bound to a substrate via a cleavable linker is contacted with a solution of peroxyanions to result in cleavage of the polynucleotide from the substrate, wherein the peroxyanions have a pKa within the range 4-12, at neutral to mildly basic pH (e.g. the pH typically is in the range from about 6 to about 11).

In typical embodiments, the conditions employed for deprotection include contacting the polynucleotide with the solution of the α-effect nucleophile for time sufficient to result in cleavage of the phosphorus protecting group. Typical times (duration) for the cleavage reaction range from about 15 minutes to about 24 hour, although times outside this range may be used. Typically, the duration of the contacting is in the range from about 30 minutes to about 16 hours, e.g., from about 45 minutes to about 12 hours, from about 1 hour to about 8 hours, or from about 1 hour to about 4 hours.

One advantage of using a neutral to mildly basic (e.g., pH in the range from about 6 to about 11) solution including an α-effect nucleophile is that the solution including an α-effect nucleophile is compatible with standard phosphoramidite methods for polynucleotide synthesis. Further, the polynucleotides released from the substrate by cleavage of the cleavable linker are stable and show little or no degradation for an extended period of time when stored in the solution including the α-effect nucleophile.

In general, the solution including the α-effect nucleophile can be a predominantly buffered aqueous solution or buffered aqueous/organic solution. Under these conditions it is convenient and cost effective to recover the released polynucleotide from the mixture of released polynucleotide and solution of α-effect nucleophile by simple precipitation of the desired polynucleotides directly from the mixture by addition of ethanol to the mixture. Under these conditions, the polynucleotide is pelleted to the bottom of a centrifuge tube and the supernatant containing the α-effect nucleophile removed by simply pouring off the supernatant and rinsing the pellet with fresh ethanol. The released polynucleotide is then isolated by resuspending in a typical buffer for chromatographic purification or direct usage in the biological experiment of interest. Because of the nature of most α-effect nucleophiles, removal from the desired released polynucleotide products is easy, quick, and effective using the ethanol precipitation method. Any other methods of recovering the polynucleotides may be employed, such as using Micro Bio-Spin™ chromatography columns (BioRad, Hercules, Calif.) for cleanup and purification of polynucleotides (used according to product insert instructions).

The solution including the α-effect nucleophile typically may have a pH in the range of about 4 to 11, about 5 to 11, about 6 to 11, about 7 to 11, about 8 to 11, about 4 to 10, about 5 to 10, about 6 to 10, about 7 to 10, or about 8 to 10. In particular embodiments the solution has a pH of about 7 to 10. It should also be noted that the pH is dependent, at least in part, upon the α-effect nucleophile in the solution and the protecting groups on the polynucleotide. Appropriate adjustments to the pH can be made to the solution to accommodate the α-effect nucleophile.

The α-effect nucleophiles can include, but are not limited to, peroxyanions, hydroxylamine derivatives, hydroximic acid and derivatives thereof, hydroxamic acid and derivatives thereof, carbazide and semicarbazides and derivatives thereof. The α-effect nucleophiles can include compounds such as, but not limited to, hydrogen peroxide, peracids, perboric acid salts, alkylperoxides, hydrogen peroxide salts, hydroperoxides, butylhydroperoxide, benzylhydroperoxide, phenylhydroperoxide, cumene hydroperoxide, performic acid, peracetic acid, perbenzoic acid and substituted perbenzoic acids such as chloroperbenzoic acid, perbutyric acid, tertiary-butylperoxybenzoic acid, decanediperoxoic acid, other similar compounds, and corresponding salts, and combinations thereof. Hydrogen peroxide, salts of hydrogen peroxide and mixtures of hydrogen peroxide and performic acid are especially useful. Hydrogen peroxide, whose pKa is around 11, is particularly useful in solutions above pH 9.0. Below pH 9.0 there is no significant concentration of peroxyanion to work as an effective nucleophile. Below pH 9.0 it is especially useful to use mixtures of hydrogen peroxide and peracids. These peracids can be preformed and added to the solution or they can be formed in situ by the reaction of hydrogen peroxide and the carboxylic acid or carboxylic acid salt. An example is that an equal molar mixture of hydrogen peroxide and sodium formate can be used at pH conditions below 9.0 as an effective α-effect nucleophile solution where hydrogen peroxide alone is not provide a high concentration of α-effect nucleophiles. The utility of peracids tends to be dependent upon the pKa of the acid and size of molecule: the higher the pKa of the acid the more useful as a peroxyanion solution, the larger the size of the molecule the less useful. Typically the pKa of the peracid is lower than the pH of the desired peroxyanion solution.

The α-effect nucleophiles typically used in these reactions are typically strong oxidants, therefore one should limit the concentration of the reagent in the solution in order to avoid oxidative side products where undesired. The α-effect nucleophiles are typically less than 30% weight/vol of the solution, more typically between 0.1% and 10% weight/vol of the solution and most typically 3% to 7% weight/vol of the solution. The typical 3% solution of hydrogen peroxide is about 1 molar hydrogen peroxide. A solution of between 1 molar and 2 molar hydrogen peroxide is typically useful. A typical solution of hydrogen peroxide and performic acid is an equal molar mixture of hydrogen peroxide and performic acid, both in the range of 1 to 2 molar. An example of an in situ prepared solution of performic acid is 2 molar hydrogen peroxide and 2 molar sodium formate buffered at pH 8.5.

In typical embodiments, the α-effect nucleophile is characterized as having a pKa in the range from about 4 to 13, about 4 to 12, about 4 to 11, about 5 to 13, about 5 to 12, about 5 to 11, about 6 to 13, about 6 to 12, about 6 to 11, about 7 to 13, about 7 to 12, or about 7 to 11.

It should also be noted that the dissociation constant (the pKa) is a physical constant that is characteristic of the specific α-effect nucleophile. Chemical substitution and solvent conditions can be used to raise or lower the effective dissociation constant and therefore specifically optimize the conditions under which the cleavage of the cleavable linker is performed (to result in release of the polynucleotide from the substrate, and, optionally, deprotection of groups protected by peroxyanion-labile protecting groups). Appropriate selection of the α-effect nucleophile should be made considering the other conditions of the method and the protecting groups of the polynucleotide. In addition, mixtures of carboxylic acids and hydroperoxides can be used to form salts of peracids in situ.

As an example a solution of hydrogen peroxide can be used with a solution of formic acid at pH conditions below 9.0. At pH conditions less than 9.0, hydrogen peroxide is not significantly ionized due to its ionization constant of around 11. At pH 7.0 only about 0.01% of the hydrogen peroxide is in the ionized form of the α-effect nucleophile. However, the hydrogen peroxide can react in situ with the formic acid to form performic acid in a stable equilibrium. At pH 7.0 the performic acid is significantly in the ionized form and is an active α-effect nucleophile. The advantage of such an approach is that solutions of performic acid tend to degrade rapidly and stabilizers need to be added. The equilibrium that is formed between the hydrogen peroxide solutions and the formic acid helps stabilize the performic acid such that it can be used to completely cleave the polynucleotides from the substrates prior to degrading. Performic acid is especially useful in a buffered mixture of hydrogen peroxide at pH 8.5 because the pKa of performic acid is approximately 7.1. Peracetic acid is useful at pH 8.5 but less useful than performic acid because the pKa of peracetic acid is approximately 8.2. At pH 8.5 peracetic acid is only about 50% anionic whereas at pH 8.5 performic acid is more than 90% anionic.

In general, the pKa for the hydroperoxides is about 8 to 13. The pKa for hydrogen peroxide is quoted to be about 10 to 12 depending upon the method of analysis and solvent conditions. The pKa for the alkylperoxides is about 8 to 14. The pKa for the peracids is about 3 to 9. In some embodiments in which the peroxyanion is hydroperoxide, the solution is at pH of about 9 to 11, e.g. at a pH of about 9 to about 10. In certain embodiments in which the peroxyanion is an alkylperoxide, the solution is at pH of about 8 to 11. In embodiments where the peroxyanion is a peracid, the solution is at pH of about 6 to 9. In addition, the peracid typically has a pKa of about 4 to 10.

In addition, the aqueous buffer solution usually includes a buffer, such as, but not limited to, tris(hydroxymethyl)aminomethane, aminomethylpropanol, citric acid, N,N'-Bis(2-hydroxyethyl)glycine, 2-[Bis(2-hydroxyethyl)amino]-2-(hydroxy-methyl)-1,3-propanediol, 2-(Cyclohexylamino) ethane-2-sulfonic acid, N-2-Hydroxyethyl)piperazine-N'-2-ethane sulfonic acid, N-(2-Hydroxyethyl)piperazine-N'-3-propane sulfonic acid, Morpholinoethane sulfonic acid, Morpholinopropane sulfonic acid, piperazine-N,N'-bis(2-ethane sulfonic acid), N-Tris(hydroxymethyl)methyl-3-aminopropane sulfonic acid, N-Tris(hydroxymethyl)methyl-2-aminoethane sulfonic acid, N-Tris(hydroxymethyl) methylglycine, and combinations thereof.

One significant potential advantage for cleaving the polynucleotide from a substrate according to the present methods is that the α-effect nucleophile solution can be exploited to remove a variety of peroxyanion-labile protecting groups at the same time and under the same conditions that are used to cleave the polynucleotide from the substrate. Thus, cleavage of the polynucleotide from the substrate and deprotection of groups protected with peroxyanion-labile protecting groups may be reduced to a single step in which the cleavage and deprotection occur at essentially the same time in the same reaction mixture. These advantages become even more significant if they are used with the protecting groups described in the applications cited herein to Dellinger et al. that were filed on the same day as the present application; such protecting groups specifically provide for rapid deprotection under the oxidative, nucleophilic conditions at neutral to mildly basic pH.

Particularly contemplated is the use of the cleavable linkers described herein in conjunction with peroxyanion-labile protecting groups attached to the polynucleotide. The peroxyanion-labile protecting groups may be attached, e.g. at the 2'-position of the nucleoside sugar of the individual nucleotide subunits, at the exocyclic amine groups of the heterocyclic bases of the polynucleotide, at the imine groups of the heterocyclic bases of the polynucleotide, and/or at the phosphate groups of the backbone of the polynucleotide. In certain such embodiments, contacting the polynucleotide with solution including an α-effect nucleophile results in concurrent cleavage of the polynucleotide from the substrate and deprotection of the polynucleotide, e.g., at the 2'-position of the nucleoside sugar, at the exocyclic amine groups, at the imine groups of the heterocyclic bases, and/or at the phosphate groups.

For example, in particular embodiments a polynucleotide bound to a substrate via a cleavable linker as described herein has peroxyanion-labile protecting groups on, e.g., the exocyclic amine groups. In some such embodiments, contacting the polynucleotide with solution including an α-effect nucleophile results in concurrent cleavage of the polynucleotide from the substrate and deprotection of the exocyclic amine groups. As another example, in particular embodiments a polynucleotide bound to a substrate via a cleavable linker as described herein has peroxyanion-labile protecting groups on, e.g., the 2' position of the nucleoside sugar. In certain such embodiments, contacting the polynucleotide with a solution including an α-effect nucleophile results in concurrent cleavage of the polynucleotide from the substrate and deprotection of the 2' position of the nucleoside sugar (e.g. resulting in a deprotected 2'-hydroxyl group). In a further example, a polynucleotide bound to a substrate via a cleavable linker has peroxyanion-labile protecting groups on, e.g., the 2' position of the nucleoside sugar and the exocyclic amine groups. In certain such embodiments, contacting the polynucleotide with a solution including an α-effect nucleophile results in concurrent cleavage of the polynucleotide from the substrate and deprotection of the 2' position of the nucleoside sugar and the exocyclic amine groups.

Structure (VII) serves to illustrate a portion of a polynucleotide bound to a substrate, and illustrates that there are several sites of the polynucleotide which may have protecting groups bound thereto, including phosphorus protecting groups (designated R in structure (VII), and sometimes referenced herein as "phosphate protecting groups"), nucleobase protecting groups (designated R" in structure (VII)); and 2'-hydroxyl protecting groups (designated R' in structure (VII), and sometimes referenced herein as 2'-O protecting groups). Note that structure (VII) only depicts two nucleotide subunits, but that typically there will be many more nucleotide subunits in the polynucleotide having the same general structure as the nucleotide subunits depicted in structure (VII). In structure (VII), B represents a nucleobase. It is contemplated that, in particular embodiments, the protecting groups (i.e., one or more of R, R', and/or R") may be labile under the same conditions that result in cleavage of the cleavable linkers (CLG in structure (VII)) described herein.

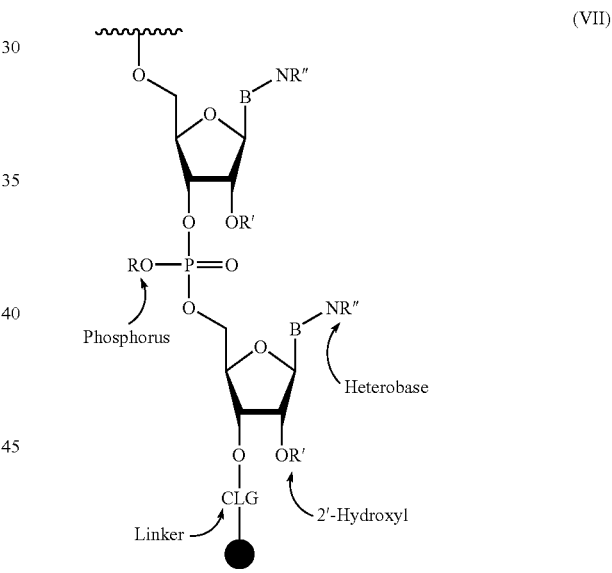

(VII)

In particular embodiments the polynucleotide has a plurality of phosphate groups wherein each phosphate group is bound to a phosphate protecting group. In certain such embodiments, the phosphate protecting group is labile under the same conditions as the cleavable linker (e.g., the phosphate protecting group is peroxyanion-labile). Thus, the cleavable linker may be cleaved and the phosphate groups may undergo deprotection concurrently upon being contacted with a solution comprising an α-effect nucleophile. Any phosphate protecting group known in the art of polynucleotide synthesis that is labile under conditions of cleavage of the cleavable linker may be used. Examples of such phosphate protecting groups are described in a copending U.S. patent application Ser. No. 11/388,339 titled "Phosphorus Protecting Groups"; the disclosure of which is herein incorporated by reference.

Thus, in particular embodiments, the present invention provides for a method that includes: contacting a polynucleotide bound to a substrate via a cleavable linker with a solution comprising an α-effect nucleophile; wherein the polynucleotide has a plurality of phosphate groups; wherein each phosphate group of the plurality of phosphate groups has a phosphate protecting group bound thereto, said phosphate protecting group characterized as being labile upon exposure to the α-effect nucleophile, said contacting resulting in concurrent cleavage of the polynucleotide from the substrate and deprotection of each phosphate group of the plurality of phosphate groups.

In particular embodiments the polynucleotide has a plurality of nucleobases, wherein each nucleobase is bound to a nucleobase protecting group. In certain such embodiments, the nucleobase protecting group is labile under the same conditions as the cleavable linker (e.g. the nucleobase protecting group is peroxyanion-labile). Thus, the cleavable linker may be cleaved and the nucleobases may undergo deprotection concurrently upon being contacted with a solution comprising an α-effect nucleophile. Any nucleobase protecting group known in the art of polynucleotide synthesis that is labile under conditions of cleavage of the cleavable linker may be used. Examples of such nucleobase protecting groups are described in a copending application Ser. No. 11/387,388 titled: "Monomer Compositions for the Synthesis of Polynucleotides, Methods of Synthesis, and Methods of Deprotection"; the disclosure of which is herein incorporated by reference.

Thus, in particular embodiments, the present invention provides for a method that includes: contacting a polynucleotide bound to a substrate via a cleavable linker with a solution comprising an α-effect nucleophile; wherein the polynucleotide has a plurality of nucleobases; wherein each nucleobase of the plurality of nucleobases has a nucleobase protecting group bound thereto, said nucleobase protecting group characterized as being labile upon exposure to the α-effect nucleophile, said contacting resulting in concurrent cleavage of the polynucleotide from the substrate and deprotection of each nucleobase of the plurality of nucleobases.

In particular embodiments the polynucleotide has a plurality of 2'-O groups wherein each 2'-O group is bound to a 2'-O protecting group (i.e., a 2'-hydroxyl protecting group). In certain such embodiments, the 2'-O protecting group is labile under the same conditions as the cleavable linker (e.g. the 2'-O protecting group is peroxyanion-labile). Thus, the cleavable linker may be cleaved and the 2'-O groups may undergo deprotection concurrently upon being contacted with a solution comprising an α-effect nucleophile. Any 2'-O protecting group known in the art of polynucleotide synthesis that is labile under conditions of cleavage of the cleavable linker may be used. Examples of such 2'-O protecting groups are described in a copending application Ser. No. 11/388,112 titled "Monomer Compositions for the Synthesis of Polynucleotides, Methods of Synthesis, and Methods of Deprotection" and designated; the disclosure of which is herein incorporated by reference.

Thus, in particular embodiments, the present invention provides for a method that includes: contacting a polynucleotide bound to a substrate via a cleavable linker with a solution comprising an α-effect nucleophile; wherein the polynucleotide has a plurality of 2'-O groups; wherein each 2'-O group of the plurality of 2'-O groups has a 2'-O protecting group bound thereto, said 2'-O protecting group characterized as being labile upon exposure to the α-effect nucleophile, said contacting resulting in concurrent cleavage of the polynucleotide from the substrate and deprotection of each 2'-O group of the plurality of 2'-O groups.

Furthermore, in certain embodiments, the polynucleotide includes a plurality of phosphate groups, a plurality of nucleobases, and a plurality of 2'-O groups. In some embodiments, the polynucleotide also includes one or more (e.g., two or more, e.g., all three) types of protecting groups selected from phosphate protecting groups, nucleobase protecting groups, or 2'-O protecting groups. Each protecting group is bound to a corresponding site of the polynucleotide (i.e., phosphate protecting groups are bound to phosphate groups, nucleobase protecting groups are bound to nucleobases, and 2'-O protecting groups are bound to 2'-O groups). In certain embodiments, the method provides for deprotection of the polynucleotide and concurrent cleavage of the polynucleotide from the substrate. The concurrent deprotection and cleavage may include deprotection of: 1) the phosphate groups 2) the nucleobases, 3) the 2'-O groups; 4) phosphate groups and the nucleobases, 5) the nucleobases and the 2'-O groups, 6) phosphate groups and the 2'-O groups; or 7) the phosphate groups, the nucleobases, and the 2'-O groups.

In certain embodiments, the polynucleotide has a 2'-hydroxyl protecting group and at least one additional protecting group selected from a nucleobase protecting group and/or a phosphorus protecting group, wherein the 2'-hydroxyl protecting group is stable under conditions which include an α-effect nucleophile. In this regard, "stable" means that the protecting group is not susceptible to being cleaved (removed from the protected group) upon being contacted with an α-effect nucleophile. However, in these embodiments, the nucleobase protecting group and/or a phosphorus protecting group are labile under conditions which include an α-effect nucleophile; thus, the contacting with the solution of α-effect nucleophile results in concurrent cleavage of the polynucleotide from the substrate and cleavage of said nucleobase protecting groups and/or a phosphorus protecting groups. In some such embodiments, the method further provides for cleaving the 2'hydroxyl protecting group under conditions sufficient to result in cleavage of the 2'hydroxyl protecting group, wherein said conditions do not include α-effect nucleophile. The cleaving of the 2'hydroxyl protecting group in such embodiments may be either before or after the contacting with α-effect nucleophile (i.e., before or after the concurrent cleavage of the cleavable linker and nucleobase protecting group and/or a phosphorus protecting group).

In certain embodiments, the polynucleotide has a 2'-hydroxyl protecting group, a phosphorus protecting group, and a nucleobase protecting group; wherein the 2'-hydroxyl protecting group and phosphorus protecting group are stable under conditions which include an α-effect nucleophile. In these embodiments, the nucleobase protecting group is labile under conditions which include an α-effect nucleophile; thus the contacting with the solution of α-effect nucleophile results in concurrent cleavage of the polynucleotide from the substrate and cleavage of said nucleobase protecting group. In some such embodiments, the method further provides for cleaving the 2'-hydroxyl protecting group and/or the phosphorus protecting group under conditions sufficient to result in cleavage of the 2'-hydroxyl protecting group and/or the phosphorus protecting group, wherein said conditions do not include α-effect nucleophile. The cleaving of the 2'-hydroxyl protecting group and/or the phosphorus protecting group in such embodiments may be before or after the contacting with α-effect nucleophile (i.e., before or after the concurrent cleavage of the cleavable linker and nucleobase protecting group)

Aspects of the invention further include the nucleic acid products of the methods of the invention. The nucleic acid products, e.g., RNA, DNA, of the methods of the invention may vary in size, ranging in certain embodiments from 2 to 200 or more monomeric units in length, such as 2 to 100 or more monomeric units in length, including 2 to 50 or more monomeric units in length. In certain embodiments, the size of the product nucleic acids ranges from 2 to 25 monomeric units in length, e.g., 20 to 25 monomeric units in length.

The product nucleic acids find use in a variety of applications, including research, diagnostic and therapeutic applications. For example, the product nucleic acids find use in research applications, e.g., as probes, primers, etc. With respect to diagnostic applications, the product nucleic acids may also find use as probes, primers, or other agents employed in diagnostic protocols. With respect to therapeutic applications, the product nucleic acids find use as any DNA, RNA or other nucleic acid therapeutic, such as antisense nucleic acids, in gene therapy applications, interfering RNA (i.e., iRNA or RNAi) applications, etc.

Depending on the application for which the nucleic acids are synthesized, the nucleic acids may or may not be modified in some manner following their synthesis. As such, in certain embodiments the product nucleic acids are not further modified following synthesis. In yet other embodiments, the nucleic acids are modified in some manner following their synthesis.

A variety of different modifications may be made to the product nucleic acids as desired. For example, where the product nucleic acids are interfering ribonucleic acids (iRNA), a variety of post-synthesis modifications may be desirable. The iRNA agent can be further modified so as to be attached to a ligand that is selected to improve stability, distribution or cellular uptake of the agent, e.g., cholesterol. The following post-synthesis modifications are described for convenience primarily in terms of iRNA embodiments. However, such modifications are readily adapted to DNA embodiments and the following description encompasses such embodiments as well.

The following modifications may be made before or after cleavage of the nucleic acid from the support, as desired.

Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) Nucleic Acids Res. 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking 0 of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. For example, a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g., pharmacodynamic properties, which are further discussed below. Other suitable modifications to a sugar, base, or backbone of an iRNA agent are described in PCT Application No. PCT/US2004/01193, filed Jan. 16, 2004. An iRNA agent can include a non-naturally occurring base, such as the bases described in PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in PCT Application No. PCT/US2004/07070 filed on Mar. 8, 2004.

An iRNA agent can include ligand-conjugated monomer subunits and monomers for oligonucleotide synthesis. Exemplary monomers are described in U.S. application Ser. No. 10/916,185, filed on Aug. 10, 2004. An iRNA agent can have a ZXY structure, such as is described in PCT Application No. PCT/US2004/07070 filed on Mar. 8, 2004. An iRNA agent can be complexed with an amphipathic moiety. Exemplary amphipathic moieties for use with iRNA agents are described in PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane);

and (c) a targeting group, e.g., a cell or tissue targeting agent, e.g., a lectin, glycoprotein, lipid or protein, e.g., an antibody, that binds to a specified cell type. iRNA agents complexed to a delivery agent are described in PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in PCT Application No. PCT/US2004/07070 filed on Mar. 8, 2004.

An iRNA agent can have enhanced resistance to nucleases. For increased nuclease resistance and/or binding affinity to the target, an iRNA agent, e.g., the sense and/or antisense strands of the iRNA agent, can include, for example, 2'-modified ribose units and/or phosphorothioate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

One way to increase resistance is to identify cleavage sites and modify such sites to inhibit cleavage, as described in U.S. Application No. 60/559,917, filed on May 4, 2004. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3'C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In one embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In certain embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization may be used only in terminal regions, and not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In certain embodiments, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

The properties of an iRNA agent, including its pharmacological properties, can be influenced and tailored, for example, by the introduction of ligands, e.g. tethered ligands. A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Of interest are ligands, which are coupled, e.g., covalently, either directly or indirectly via an intervening tether, to the carrier. In certain embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_nNH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In certain embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Ligands of interest can improve transport, hybridization, and specificity properties and may also improve nuclease resistance of the resultant natural or modified oligoribonucleotide, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic molecules, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. Also of interest are the lipid modifications described in WO/2005/023994; the disclosure of which is herein incorporated by reference.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

In certain embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Where desired, the nucleic acid, e.g., iRNA, DNA, etc, agents described herein can be formulated for administration to a subject, such as parenterally, e.g. via injection, orally, topically, to the eye, etc. As such, the nucleic acid can be combined with a pharmaceutically acceptable vehicle to provide a pharmaceutical composition. For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation. The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as Mg24), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same gene but different target sequences.

The nucleic acids can be formulated into pharmaceutical compositions by combination with appropriate, pharmaceutically acceptable vehicles, i.e., carriers or diluents, and may be formulated into preparations in solid, semi solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Nucleic acids may also be introduced into tissues or host cells by other routes, including microinjection, or fusion of vesicles. Jet injection may also be used for intra-muscular administration, as described by Furth et al. (1992), Anal Biochem 205:365-368. The nucleic acids may be coated onto gold microparticles, and delivered intradermally by a particle bombardment device, or "gene gun" as described in the literature (see, for example, Tang et al. (1992), Nature 356:152 154), where gold microprojectiles are coated with the DNA, then bombarded into skin cells. Additional nucleic acid delivery protocols of interest include, but are not limited to: those described in U.S. patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc. See e.g., the viral and non-viral mediated delivery protocols described above. Accordingly, of interest are pharmaceutical vehicles for use in such delivery methods.

EXPERIMENTAL

The practice of the present invention will employ, unless otherwise indicated, conventional techniques of synthetic organic chemistry, biochemistry, molecular biology, and the like, which are within the skill of the art. Such techniques are explained fully in the literature.

The present specification is put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, percents are wt./wt., temperature is in ° C. and pressure is at or near atmospheric. Standard temperature and pressure are defined as 20° C. and 1 atmosphere.

A synthesis of reagents used in certain embodiments of the present invention is now described. It will be readily apparent that the reactions described herein may be altered, e.g. by using modified starting materials to provide correspondingly modified products, and that such alteration is within ordinary skill in the art. Given the disclosure herein, one of ordinary skill will be able to practice variations that are encompassed by the description herein without undue experimentation.

Synthesis of 5'-O-Dimethoxytrityl-2'-O-tert-butylthiocarbonate-3'-O-(4-nitrophenyl) carbonate uridine 5'-O-Dimethoxytrityl-2'-O-tert-butylthiocarbonate uridine (0.5 mmole) was coevaporated 3 times with pyridine, and then dried on vacuum pump for 2 hours. Anhydrous pyridine (5 mL) and 4-nitrophenyl chloroformate (153 mg, 0.75 mmole) were added, and the mixture was stirred at room temperature for 16 hours. Product was purified by flash chromatography using hexanes:Py (99.9:0.1) with a gradient of ethyl acetate (0-40%). The yield was 46%.

Preparation of TENTA Gel Solid Support with Thiocarbonate Linker:

TENTA GEL thio resin (1 g) (Rapp Polymere GmbH, Tubingen, Germany) and 5'-O-Dimethoxytrityl-2'-O-tert-butylthiocarbonate-3'-O-(4-nitrophenyl) carbonate uridine (148 mg, 0.7 eq) were dried separately on vacuum pump for 12 hours. Anhydrous 1,4-dioxane (5 mL) was added to TENTA GEL resin and left for 20 min. After that time 1,8-diazabicyclo[5.4.0]undec-7-ene (0.041 mL, 1.1 eq) was added and the mixture was shaken for about 5 min. Solution of 5'-O-dimethoxytrityl-2'-O-tert-butylthiocarbonate-3'-O-(4-nitrophenyl) carbonate uridine in anhydrous 1,4-dioxane (2 mL) was then added. The flask was tightly capped and shaken for 3 days. Solid support was filtered off and washed successively with dioxane, methanol, and DCM, and then dried on vacuum pump. The loading of the obtained solid support was 28.3 micromole/g.

The result is a single nucleoside moiety bound to the substrate via a cleavable linker; wherein the cleavable inker has the structure (I) as described above. The single nucleoside moiety has a 5'-hydroxyl protecting group. Removal of the 5'-hydroxyl protecting group provides an initial hydroxyl to which a nucleoside phosphoramidite may be coupled in the first step of a standard polynucleotide synthesis method. Synthesis of a polynucleotide may be performed, and the synthesized polynucleotide will be attached to the substrate via the cleavable linker.

Synthesis of a $(dT)_8$ polynucleotide was performed on a TENTA GEL solid support with a cleavable linker, giving the following product:

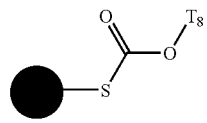

(wherein the solid circle represents the TENTA GEL).

The product was then contacted with 5% hydrogen peroxide (pH 9.4, 50 mM alkaline buffer, 10% methanol) for approximately 30 minutes. The crude cleavage mixture was analysed using reverse phase-HPLC on a HYPERSYL column (Hypersil, Holliston, Mass.), eluted with TEAAc/acetonitrile.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

What is claimed is:

1. A method comprising:
contacting a polynucleotide bound to a substrate via a cleavable linker with a solution comprising an α-effect nucleophile to result in cleavage of the polynucleotide from the substrate to produce a free polynucleotide; wherein the cleavable linker has the structure (I):

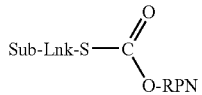
(I)

wherein:
Lnk is a linking group;
Sub denotes the site at which the substrate is attached to the cleavable linker; and
RPN denotes the site at which the polynucleotide is attached to the cleavable linker; and
chemically modifying said free polynucleotide to produce a modified free polynucleotide.

2. The method of claim 1, wherein the solution is at a pH of about 6 to about 12.

3. The method of claim 1, wherein the α-effect nucleophile is characterized as having a pKa in the range of about 4 to 13.

4. The method of claim 1, wherein the solution comprising the α-effect nucleophile is a solution comprising one or more species selected from hydrogen peroxide, salts of hydrogen peroxide, and mixtures of hydrogen peroxide and performic acid.

5. The method of claim 1, wherein the linking group Lnk is selected from:
(1) a lower alkyl group;
(2) a modified lower alkyl group in which one or more linkages selected from ether-, thio-, amino-, keto-, ester-, phospho- and amido- is present;
(3) a modified lower alkyl substituted with one or more groups including lower alkyl; aryl, aralkyl, alkoxyl, thioalkyl, hydroxyl, amino, amido, sulfonyl, halo; or
(4) a modified lower alkyl substituted with one or more groups including lower alkyl; alkoxyl, thioalkyl, hydroxyl, amino, amido, sulfonyl, halo, and in which one or more linkages selected from ether-, thio-, amino-, keto-, ester-, and amido- is present.

6. The method of claim 1, wherein the linking group Lnk has the structure

wherein:
m and n are integers independently selected from the range of 1 to about 12, and
Lkg is a linkage selected from ether-, thio-, amino-, keto-, ester-, or amido.

7. The method of claim 1, wherein the polynucleotide comprises at least one protecting group selected from a nucleobase protecting group, a 2'-hydroxyl protecting group, and a phosphate protecting group, wherein said at least one protecting group is labile under conditions which include an α-effect nucleophile; and wherein said contacting results in concurrent cleavage of the polynucleotide from the substrate and deprotection of the polynucleotide.

8. The method according to claim 1, wherein said method further comprises combining said modified free polynucleotide with a pharmaceutically acceptable vehicle.

9. The method according to claim 1, wherein said polynucleotide is a DNA.

10. The method according to claim 1, wherein said polynucleotide is a RNA.

11. A method comprising:
contacting a polynucleotide bound to a substrate via a cleavable linker with a solution comprising an α-effect nucleophile to result in cleavage of the polynucleotide from the substrate to produce a free polynucleotide; wherein the cleavable linker has the structure (I):

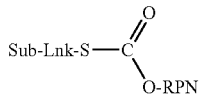
(I)

wherein:
Lnk is a linking group;
Sub denotes the site at which the substrate is attached to the cleavable linker; and
RPN denotes the site at which the polynucleotide is attached to the cleavable linker; and
combining said free polynucleotide with a pharmaceutically acceptable vehicle.

12. The method of claim 11, wherein the solution is at a pH of about 6 to about 12.

13. The method of claim 11, wherein the α-effect nucleophile is characterized as having a pKa in the range of about 4 to 13.

14. The method of claim 11, wherein the solution comprising the α-effect nucleophile is a solution comprising one or more species selected from hydrogen peroxide, salts of hydrogen peroxide, and mixtures of hydrogen peroxide and performic acid.

15. The method of claim 11, wherein the linking group Lnk is selected from:
(1) a lower alkyl group;
(2) a modified lower alkyl group in which one or more linkages selected from ether-, thio-, amino-, keto-, phosphor ester-, and amido- is present;
(3) a modified lower alkyl substituted with one or more groups including lower alkyl; aryl, aralkyl, alkoxyl, thioalkyl, hydroxyl, amino, amido, sulfonyl, halo; or
(4) a modified lower alkyl substituted with one or more groups including lower alkyl; alkoxyl, thioalkyl, hydroxyl, amino, amido, sulfonyl, halo, and in which one or more linkages selected from ether-, thio-, amino-, keto-, ester-, and amido- is present.

16. The method of claim 11, wherein the linking group Lnk has the structure

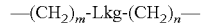

wherein:
m and n are integers independently selected from the range of 1 to about 12, and
Lkg is a linkage selected from ether-, thio-, amino-, keto-, ester-, or amido.

17. The method of claim 11, wherein the polynucleotide comprises at least one protecting group selected from a nucleobase protecting group, a 2'-hydroxyl protecting group, and a phosphate protecting group, wherein said at least one protecting group is labile under conditions which include an α-effect nucleophile; and wherein said contacting results in concurrent cleavage of the polynucleotide from the substrate and deprotection of the polynucleotide.

18. The method according to claim 11, wherein said method further comprises chemically modifiying said free polynucleotide to produce a modified free polynucleotide.

19. The method according to claim 11, wherein said polynucleotide is a DNA.

20. The method according to claim 11, wherein said polynucleotide is an RNA.

21. A polynucleotide produced according to the method of claim 1.

22. A polynucleotide produced according to the method of claim 11.

23. The method of claim 1, further comprising:
prior to said contacting:
synthesizing said synthetic polynucleotide by a sequential addition of nucleotide monomers to a nucleotide or nucleoside monomer that is covalently bound to said substrate via said cleavable linker.

24. The method of claim 11, further comprising:
prior to said contacting:
synthesizing said polynucleotide by a sequential addition of nucleotide monomers to a nucleotide or nucleoside monomer that is covalently bound to said substrate via said cleavable linker.

25. The method of claim 1, wherein:
RPN is a 2'-, 3'- or 5'-position of a terminal nucleotide of the polynucleotide; and
wherein the cleaved polynucleotide comprises a hydroxyl group at the 2'-, 3'- or 5'-position of the terminal nucleotide.

26. The method of claim 11, wherein:
RPN is a 2'-, 3'- or 5'-position of a terminal nucleotide of the polynucleotide; and
wherein the cleaved polynucleotide comprises a hydroxyl group at the 2'-, 3'- or 5'-position of the terminal nucleotide.

* * * * *

UNITED STATES PATENT AND TRADEMARK OFFICE
CERTIFICATE OF CORRECTION

PATENT NO. : 7,790,387 B2  Page 1 of 1
APPLICATION NO. : 11/903821
DATED : September 7, 2010
INVENTOR(S) : Douglas J. Dellinger et al.

It is certified that error appears in the above-identified patent and that said Letters Patent is hereby corrected as shown below:

In column 28, lines 41-42, in Claim 15, delete "phosphor" and insert -- phospho-, --, therefor.

In column 29, line 2, in Claim 18, delete "modifiying" and insert -- modifying --, therefor.

Signed and Sealed this

Twenty-third Day of November, 2010

David J. Kappos
*Director of the United States Patent and Trademark Office*